United States Patent
Rey et al.

(10) Patent No.: US 9,387,166 B2
(45) Date of Patent: Jul. 12, 2016

(54) CONTROLLED RELEASE ORAL DOSAGE FORM COMPRISING OXYCODONE

(75) Inventors: Hélène Rey, Rosenau (FR); Marc Fischer, Hagenthal le Bas (FR); Mathias Scheer, Wehr (DE); Dirk Kramer, Herznach (CH)

(73) Assignee: DEVELCO PHARMA SCHWEIZ AG, Pratteln (CH)

( * ) Notice: Subject to any disclaimer, the term of this patent is extended or adjusted under 35 U.S.C. 154(b) by 0 days.

(21) Appl. No.: 14/129,265

(22) PCT Filed: Jun. 29, 2012

(86) PCT No.: PCT/EP2012/002739
§ 371 (c)(1),
(2), (4) Date: Feb. 14, 2014

(87) PCT Pub. No.: WO2013/000578
PCT Pub. Date: Jan. 3, 2013

(65) Prior Publication Data
US 2014/0377349 A1    Dec. 25, 2014

(30) Foreign Application Priority Data

Jun. 30, 2011 (EP) .................................. 11005365

(51) Int. Cl.
*A61K 9/00* (2006.01)
*A61K 9/16* (2006.01)
*A61K 9/20* (2006.01)
*A61K 9/50* (2006.01)
*A61K 31/485* (2006.01)

(52) U.S. Cl.
CPC ............. *A61K 9/0053* (2013.01); *A61K 9/1676* (2013.01); *A61K 9/2022* (2013.01); *A61K 9/2054* (2013.01); *A61K 9/2081* (2013.01); *A61K 31/485* (2013.01); *A61K 9/5047* (2013.01); *A61K 9/5078* (2013.01)

(58) Field of Classification Search
CPC . A61K 31/485; A61K 9/0053; A61K 9/1676; A61K 9/2022; A61K 9/2054; A61K 9/2081; A61K 9/5047; A61K 9/5078
See application file for complete search history.

(56) References Cited

U.S. PATENT DOCUMENTS

| 2004/0170680 A1* | 9/2004 | Oshlack et al. ............... 424/457 |
| 2005/0074493 A1 | 4/2005 | Mehta et al. |
| 2008/0317849 A1* | 12/2008 | Christgau et al. ............. 424/464 |

FOREIGN PATENT DOCUMENTS

| EP | 0631781 A1 | 1/1995 |
| EP | 1438959 A1 | 7/2004 |
| WO | WO02087512 A2 | 11/2003 |
| WO | WO03092648 A1 | 11/2003 |

(Continued)

OTHER PUBLICATIONS

New Zealand Data Sheet, Oxycontin® tablets, Oct. 2, 2014—13 pages.*

(Continued)

*Primary Examiner* — Aradhana Sasan
(74) *Attorney, Agent, or Firm* — Hylton-Rodic Law PLLC (57) ABSTRACT

The present invention relates to a controlled-release oral dosage form for administration of oxycodone once a day and a method of preparing a controlled-release oral dosage form for administration of oxycodone once a day.

11 Claims, 7 Drawing Sheets

(56) References Cited

FOREIGN PATENT DOCUMENTS

WO      WO03101384 A2    12/2003
WO      WO2009036812 A1    3/2009

OTHER PUBLICATIONS

Bauer, K.H., et al., Lehrbuch der Pharmazeutischen Technologie: Mit einer Einführung in die Bioph, Grundlagen und Methoden, (2006), pp. 210-214, Chapter 7, Stuttgart, Germany.

Güttler, K., Impact of Pharmacology and Galenics on Duration of Drug Effect and Analgesic Effectivity, TumorDiagn u Ther., 31:S7-S11 (2010).

Güttler, K., Opioidwirkungen-Die Galenik macht den Unterschied, Anästhesiol Intensivmed Notfallmed Schmerzther, 47: 224-230 (2012).

Rowe, R.C., et al., Handbook of Pharmaceutical Excipients, 5th ed., pp. 120-123, Pharmaceutical Press and American Pharmacist Assn. (2006).

* cited by examiner

Figure 1a Dissolution profiles for tablets containing 20 mg oxycodone at pH 2 and 4.5

Figure 1b  Dissolution profiles for tablets containing 20 mg oxycodone at pH 1.6 and 7.2

Figure 2a   Dissolution profiles for tablets containing 40 mg oxycodone at pH 2 and 4.5

Figure 2b   Dissolution profiles for tablets containing 40 mg oxycodone at pH 1.6 and 7.2

Figure 3  Dissolution profiles for tablets containing 10 mg oxycodone at pH 2 and 4.5

Figure 4

| Subject | $C_{24}$ at 96.0 hours | $C_{max}$ between 72.0 hours and 96.0 hours | Ratio $C_{24}/C_{max}$ |
|---|---|---|---|
| 1 | 1.97 | 5.05 | 0.39 |
| 2 | 2.12 | 5.05 | 0.42 |
| 3 | 2.84 | 6.16 | 0.46 |
| 4 | 2.97 | 7.26 | 0.41 |
| 5 | 2.28 | 5.41 | 0.42 |
| 6 | 0.57 | 5.20 | 0.11 |
| 7 | 2.71 | 9.41 | 0.29 |
| 8 | 2.99 | 8.01 | 0.37 |
| 9 | 2.34 | 6.70 | 0.35 |
| 10 | 2.38 | 4.95 | 0.48 |
| 11 | 3.69 | 6.91 | 0.53 |
| 12 | 2.92 | 6.93 | 0.42 |
| 13 | 2.08 | 4.62 | 0.45 |
| 14 | 3.55 | 8.46 | 0.42 |
| 15 | 1.96 | 5.51 | 0.36 |
| 16 | 2.28 | 6.35 | 0.36 |
| 17 | 3.92 | 11.54 | 0.34 |
| 18 | 5.35 | 10.96 | 0.49 |
| 19 | 2.05 | 5.44 | 0.38 |
| 20 | 2.32 | 4.95 | 0.47 |
| 21 | 3.65 | 9.22 | 0.40 |
| 22 | 1.78 | 4.43 | 0.40 |
| 23 | 1.28 | 4.93 | 0.26 |
| 24 | 2.51 | 6.03 | 0.42 |
| 25 | 2.66 | 7.19 | 0.37 |
| 26 | 2.96 | 7.11 | 0.42 |
| 27 | 3.61 | 9.12 | 0.40 |
| 28 | 3.19 | 7.09 | 0.45 |
| 29 | 2.65 | 5.93 | 0.45 |
| 30 | 2.00 | 5.10 | 0.39 |
| 31 | 6.02 | 11.20 | 0.54 |
| 32 | 2.48 | 5.82 | 0.43 |
| 33 | 1.96 | 6.42 | 0.31 |
| 34 | 4.69 | 13.73 | 0.34 |
| 35 | 2.00 | 6.42 | 0.31 |
| 36 | 2.94 | 8.65 | 0.34 |
| arithmetic mean | 2.77 | 7.04 | 0.39 |

Figure 5

CONTROLLED RELEASE ORAL DOSAGE FORM COMPRISING OXYCODONE

The present invention relates to a controlled release oral dosage form for administration of oxycodone once a day and a method of preparing a controlled release oral dosage form for administration of oxycodone once a day.

Oxycodone is an opioid analgesic that is deemed particularly effective in the treatment of chronic pain. Currently, twice daily immediate release and twice daily extended release formulations are available on the market for oral administration. However, no controlled formulation for once daily administration is available as yet. Therefore, there is an ongoing need to provide a controlled release oral dosage form for administration of oxycodone once a day that has advantages such as reduced dosing intervals, provision of stable plasma levels and consistent pain relief over 24 hours.

Sustained release formulations containing oxycodone or opioids in general, have been the subject of numerous patent applications. A common feature to these patent applications is the requirement that the in vitro release rate of oxycodone from the controlled release formulations containing should be independent of pH. Just by way of example, it is referred to EP 0 631 781. Furthermore, it is common general knowledge that the differences between peak and trough levels of active ingredient in blood should ideally be as low as possible. Again, just by way of example, it is referred to WO 02/087512 which discloses a sustained release dosage form comprising oxycodone for oral administration to a patient on a once-a-day basis, which provides a mean ratio of the values of the plasma concentration 24 hours after administration ($C_{24}$) and the highest plasma concentration of the drug attained within the dosing interval ($C_{max}$) of 0.6 to 1.0.

The inventors of the present invention have now surprisingly found that, contrary to common presumptions, very advantageous in vivo properties can be achieved by a controlled release oral dosage form for administration of oxycodone once a day, wherein at steady state the oral dosage form provides a mean $C_{24}/C_{max}$ of less than 0.6 after oral administration and/or wherein an amount of oxycodone released by the controlled release oral dosage form at strong acidic pH (e.g. pH 1.6 to 2, preferably pH 1.6) after a time $t_1$ differs by 8% to 30% from an amount of oxycodone released at a medium acidic to neutral pH (e.g. pH 4.5 to pH 7.2, preferably pH 7.2) after the same time $t_1$, when measured according to the USP Paddle Method in 900 ml aqueous buffer at 100 rpm and at 37° C.

Hence, the present invention provides a controlled release oral dosage form for administration of oxycodone once a day, comprising a plurality of substrates comprising oxycodone or a pharmaceutically acceptable salt or solvate thereof, each substrate comprising a release control substance for controlling the release of oxy-codon or the salt or solvate thereof, wherein at steady state the oral dosage form provides a mean $C_{24}/C_{max}$ of less than 0.6 after oral administration and/or wherein an amount of oxycodone released by the controlled release oral dosage form at pH 1.6 to 2.0, preferably pH 1.6, after a time $t_1$ differs by 8% to 30% from an amount of oxycodone released at pH 4.5 to 7.2, preferably pH 7.2, after the same time $t_1$, when measured according to the USP Paddle Method in 900 ml aqueous buffer at 100 rpm.

Further, the invention provides a controlled release tablet for administration of oxycodone once a day, comprising a plurality of substrates comprising oxycodone or a pharmaceutically acceptable salt or solvate thereof, wherein each substrate comprises an oxycodone-containing core and a release control layer coated upon the core and containing a release-control substance for controlling the release of oxycodone from the substrate, the plurality of substrates being contained in an external phase of at least one pharmaceutically acceptable excipient, preferably wherein the external phase comprises at least carboxymethyl cellulose, optionally in the form of a salt, as a pharmaceutically acceptable excipient.

Preferably, the amount of oxycodone released by the controlled release oral dosage form at pH 1.6 or 2.0 after a time $t_1$ differs by 10.1% to 30%, in particular 10.5% to 30%, from an amount of oxycodone released at pH 4.5 or pH 7.2 after the same time $t_1$, when measured according to the USP Paddle Method in 900 ml aqueous buffer at 100 rpm and preferably 37° C. Alternatively, the amount of oxycodone released by the controlled release oral dosage form at pH 1.6 or 2.0 after a time $t_1$ differs by 10.1% to 25%, in particular 10.5% to 20%, from an amount of oxycodone released at pH 4.5 or pH 7.2 after the same time $t_1$, when measured according to the USP Paddle Method in 900 ml aqueous buffer at 100 rpm and preferably 37° C. The term "differs" preferably refers to an absolute difference. That means, if for example the dissolution at pH 1.6 is 10%, then the difference of 8% results in a dissolution at pH 7.2 of 18%.

The value $C_{max}$ designates the highest plasma concentration of oxycodone attained within the dosing interval and $C_{24}$ designates the plasma concentration 24 hours after administration, each under steady state conditions. For purposes of the present invention, the steady state is regarded as being reached between 72.0 hours and 96.0 hours after administration of a first oxycodone once daily dosage form, with dosage forms being taken every 24 hours.

Time $t_1$ generally is a point in time more than 5 minutes and less than 24 hours after starting of the dissolution test, preferably more than 15 minutes and less than 12 hours. Further preferred, $t_1$ can be a point in time between 30 minutes and 10 hours, in particular 60 minutes and 8 hours after starting of the dissolution test. Preferably, the $C_{24}$, $C_{max}$ and dissolution values referred to herein are based on at least three, for instance five and more preferably 12 measurements, i.e. patients in case of $C_{24}$, $C_{max}$ and measurement runs in case of dissolution values. The mean $C_{24}/C_{max}$ ratio is preferably based on 12 measurements (patients) or more (with the ratio being calculated for each patient, and then a mean of the ratios of the respective number of patients being taken, of course). As customary in the art, the mean value designates the arithmetic mean value of the ratios of the tested patient population.

Naturally, plasma oxycodone concentrations will vary from patient to patient due to individual differences in their response due to variability in terms of absorption, distribution, metabolism and excretion. It is for this reason that the mean $C_{24}/C_{max}$ ratio values are based on the at least three, for instance five and more preferably 12 measurements (patients).

The controlled release oral dosage form according to the invention is a so-called multi-particulate dosage form comprising a plurality of substrates comprising oxycodone or a pharmaceutically acceptable salt or solvate thereof, each substrate comprising a substance for controlling the release of oxycodone or the salt or solvate thereof.

From the above, it is clear that the oral dosage form according to the present invention is not an osmotic dosage form, i.e. does not utilize the principle of osmotic pressure for the delivery of the drug. Drug release from osmotic systems is typically independent of pH and thus quite in contrast to the above laid out aspect of the present invention.

Preferably, each substrate comprises an oxycodone containing core and a release control layer containing the release control substance for controlling the release of oxycodone from the substrate. Preferably, the release control layer is (physically) separate from the oxycodone containing core. The oxycodone containing core may be a core which contains oxycodone and excipients. In those embodiments, the excipients preferably do not substantially retard or delay the release of the oxycodone.

Preferably, the core comprises a layer of oxycodone on an inert core. The inert core (also referred to as seed core or neutral pellet) may be granules or beads, preferably spherical, and further preferably made from sugar or cellulose or other suitable materials. By way of example, spherical inert cores based on saccharose, such as those commercially available under the trade name Suglets®, or those based on cellulose, such as those commercially available under the trade name Celphere® or Cellets® may be mentioned. Saccharose-based inert cores are particularly preferred. Inert cores may preferably have a particle size in the range of 100 to 500 µm and more preferably in the range of 200 to 400 µm, with the particle size range indicating the size range for 90% of the particles as determined by sieve analysis.

Preferably, oxycodone is provided by coating an oxycodone-containing layer directly onto the inert cores. The oxycodone-containing layer preferably does not delay release of oxycodone, i.e. is an immediate-release layer.

Preferably, a suitable oxycodone-containing core comprises 10 to 50 wt. %, preferably 20 to 40 wt. %, more preferably 25 to 35 wt. % neutral pellets, 20 to 90 wt. %, preferably 35 to 80 wt. %, more preferably 50 to 70 wt. % oxycodone, in particular oxycodone hydrochloride, 0.1 to 20 wt. %, preferably 1 to 15 wt. %, more preferably 3 to 8 wt. % binder, and optionally 0 to 20 wt. %, preferably 1 to 15 wt. %, more preferably 3 to 8 wt. % glidant, based on the total weight of the oxycodone containing core.

Generally, binders as described below can be used. In particular, HPMC is used as binder in the oxycodone-containing core. Preferably, said HPMC has a methoxy content of 25% to 35%, more preferably 28% to 30%. Further, preferably said HPMC has a hydroxypropoxy content of about 5% to 15%, more preferably 7% to 12%. Preferably, a 2% by weight (aqueous) solution of said HPMC has a viscosity of 0.5 to 100 mPa·s, preferably 1 to 50 mPas, more preferably 2 to 10 mPa·s, in particular 3 to 8 mPa·s, measured at 20° C., preferably by means of a Brookfield-Synchro-Lectric LVF viscosimeter.

Generally, glidants as described below can be used. In particular, talcum is used as glidant in the oxycodone-containing core.

The release control layer may be disposed in direct vicinity, i.e. in immediate contact with and surrounding the oxycodone containing core, which is preferred. In other exemplary embodiments, an intermediate layer may be disposed between the oxycodone containing core and the release control layer. This intermediate layer may further control the release of oxycodone from the core. However, it is preferred that, if present, the intermediate layer does not substantially influence the release from the core.

The release control substance may be any substance known in the art as suitable to control the release of an active substance. Exemplary embodiments of suitable control release substances include cellulose esters, such as cellulose acetate phthalate, polyvinyl pyrrolidone, polyvinyl alcohol, polyvinyl acetate, polyvinyl chloride, nylon, polyamide, polyethylene oxide, polylactide-co-glycolide and mixtures thereof. Preferably, the release control substance is a hydrophobic polymer. Suitable hydrophobic polymers include those selected from alkylcelluloses, in particular cellulose ethers, polymers and copolymers based on acrylate or methacrylate, polymers and copolymers based on acrylic or methacrylic esters and mixtures thereof. Preferably, the release control substance is an alkyl cellulose. More preferably, the alkyl cellulose is ethyl cellulose.

In exemplary embodiments of the present invention wherein the release control substance is a polymer, said polymer has a weight average molecular weight of from 5,000 to 500,0000 g/mol, preferably 50,000 to 900,000 g/mol, more preferably from 100,000 to 400,000 g/mol, for instance from 140,000 to 300,000 g/mol. The weight average molecular weight is preferably determined by gel permeation chromatography.

In further embodiments, and in addition or in the alternative to one or more of the properties mentioned above, the release control substance, and in particular the polymer, preferably has a solubility in water of less than 20 mg/l, preferably less than 15 mg/l, preferably between 0.001 to 10.0 mg/l. The solubility in water is preferably determined in accordance with European Regulation RL67-548 EWG, Annex V, Chapter A6 (Ger-man version referred to and referenced herein).

In further embodiments where a polymer is used as or as part of the release control substance, and in addition or in the alternative to one or more of the properties mentioned above, the polymer has a glass transition temperature of 20 to 220° C., for instance 60 to 150° C. or 90 to 140° C. The glass transition temperature is preferably measured by means of differential scanning calorimetry DSC, preferably using a Mettler Toledo instrument and a preferably applying a heating/cooling rate of 10° C. per minute.

In a particular preferred embodiment the release-control substance is ethylcellulose having an ethoxyl content of about 35 to 65%, more preferred of about 45 to 55%. Preferably, a 2% by weight (aqueous) solution of ethylcellulose has a viscosity of 5 to 500 mPa·s, preferably 10 to 100 mPa·s, in particular 25 to 55 mPa·s measured at 25° C., preferably by means of a Brookfield-Synchro-Lectric LVF viscosimeter.

In exemplary embodiments, the release control substance is contained in an amount of from 0.1 to 80% by weight of the total weight of the plurality of substrates in the dosage form, more preferably in amounts from 0.5 to 60% by weight, 10 to 50% by weight, 15 to 40% by weight, 20 to 30% by weight of the total weight of the plurality of substrates in the dosage form.

Control of the release rate can be adapted by appropriate selection of the control release substance or mixture of such substances, its/their amount, coating thickness, inclusion of further excipients, such as pore formers and/or plasticizers or others.

In accordance with one aspect of the present invention, the release control substance or mixture thereof and/or the release control layer and/or an external phase wherein the plurality of substrates may be contained, optionally in combination with additional release control layers, is chosen and adapted such that the pH dependence of the controlled release oral dosage form is in the indicated range, in particular wherein an amount of oxycodone released by the controlled release oral dosage form at pH 1.6 after a time $t_1$ differs by 8% to 30%, preferably 10.1% to 30%, more preferably 10.5% to 30% from an amount of oxycodone released at pH 7.2 after the same time $t_1$, when measured according to the USP Paddle Method in 900 ml aqueous buffer at 100 rpm and at 37° C. As mentioned above, alternatively, the difference in dissolution may also be determined at pH 2.0 (as the lower pH) and 4.5 (as the higher pH).

In a particularly preferred embodiment, the overall pH dependence (measured according to the conditions set out before) of the oral dosage form is due to (or substantially, respectively predominantly due to) at least one excipient in the external phase of the oral dosage form, in particular tablet, wherein the plurality of substrates is contained, whereas a dissolution profile (measured according to the conditions set out before) of the plurality of substrates is substantially independent of pH, i.e. shows less than 8%, more preferably less than 7, 6, 5, 4, 3, 2 or even 1% deviation at any point in time between the weight percentage of oxycodone dissolved at pH 1.6 or 2.0 compared to the weight percentage dissolved at the same time at pH 4.5 or 7.2.

According to this aspect, the present invention provides a controlled-release tablet for administration of oxycodone once a day, comprising a plurality of substrates comprising oxycodone or a pharmaceutically acceptable salt or solvate thereof, wherein each substrate comprises an oxycodone-containing core and a release-control layer coated upon the core and containing a release-control substance for controlling the release of oxycodone from the substrate, the plurality of substrates being contained in an external phase of at least one pharmaceutically acceptable excipient, wherein the release-control layer is adapted to release the oxycodone in a substantially pH independent manner whereas the external phase shows a pH-dependent dissolution profile, with the terms pH dependent and independent being as set out before.

Further to the release control substance, one or more additional excipients may be used, in particular in a release control layer. A preferred excipient for use with the release control substance, in particular a polymeric release control substance, is a plasticizer and/or a pore builder.

A plasticizer, as the term is used herein, is a substance that typically lowers the glass transition temperature of the polymer it is used in admixture with by at least 2° C., preferably at least 5° C., for instance between 5 and 30° C., as compared to the polymer alone. A preferred plasticizer is propylene glycol, in particular for use with ethylcellulose.

A pore former usually is a substance having a water-solubility which is higher than the water solubility of the release-control substance. Preferably, the pore former has a solubility in water of more than 20 mg/l, preferably 50 mg/l to 5000 mg/l, more preferably 100 to 1000 mg/l. The solubility in water is preferably determined as described above. In particular, hydroxypropyl cellulose (HPC) is used as pore former. Preferably, said HPC has a hydroxypropoxy content of about 50 to 95%, more preferably 70 to 80%. Preferably, a 10% by weight (aqueous) solution of said HPC has a viscosity of 10 to 3000 mPa·s, preferably 100 to 1000 mPa·s, in particular 300 to 600 mPa·s, measured at 25° C., preferably by means of a Brookfield-Synchro-Lectric LVF viscosimeter.

In a preferred embodiment, the release control layer comprises 20 to 95 wt. %, preferably 40 to 80 wt. %, more preferably 50 to 70 wt. % release control substance, preferably as described above, 0.1 to 30 wt. %, preferably 1 to 25 wt. %, more preferably 5 to 20 wt. % pore builder, preferably as described above, 0.1 to 30 wt. %, preferably 1 to 25 wt. %, more preferably 5 to 20 wt. % plasticiser, preferably as described above, and optionally 0 to 40 wt. %, preferably 5 to 30 wt. %, more preferably 10 to 25 wt. % glidant, preferably as described above, based on the total weight of the release control layer.

The release control layer may be a single layer or a plurality of layers. For ease of fabrication, embodiments with a single release control layer are preferred.

The plurality of substrates may be used as a pharmaceutical formulation in granular form, for instance, without any further processing. For this kind of administration, the substrates are preferably filled into sachets. In the alternative, they may be incorporated into capsules, optionally together with one or more excipients, or other suitable ingestible pharmaceutical dosage forms.

Most preferably, the plurality of substrates is contained in an external phase of at least one pharmaceutically acceptable excipient. Furthermore, the controlled release oral dosage form is preferably a tablet.

As evident from what has been set out before, most preferably, the oral dosage form according to the present invention does not contain any oxycodone in immediate-release form, i.e. does not contain oxycodone the release of which is not controlled by the release-control substance(s). For instance, a tablet comprising the plurality of controlled-release oxycodone substrates does not comprise any further oxycodone in the external phase.

In particularly preferred embodiments, the plurality of substrates is contained in a so-called "external phase". The external phase preferably comprises carboxymethyl cellulose, in particular sodium carboxymethyl cellulose, as a pharmaceutically acceptable excipient. Carboxymethyl cellulose may be used as such or in the form of one of its salts, for instance sodium salt, calcium salt or a combination thereof. Carboxymethyl cellulose sodium salts are particularly preferred, in particular those designated "Carmellose sodium" or "low substituted carmellose sodium" according to Ph. Eur. 6.0. Preferably, the sodium content is in the range of 1 to 15% by weight, based on the total weight of the carmellose sodium salt. Enzymatically hydrolysed carboxymethyl cellulose (E 469) shall be equally encompassed by the term carboxymethyl cellulose. In the following, it will be simply referred to carboxymethyl cellulose, with the salts being included in the meaning of the term, for ease of reference.

Preferably, the carboxymethyl cellulose is not cross-linked. Further preferably, a 2% by weight (aqueous) solution of carboxymethyl cellulose has a viscosity of 50 to 4500 mPa·s, preferably 100 to 3000 mPa·s, in particular 120 to 2000 mPa·s and in further embodiments 150 to 1500 mPa·s, measured at 25° C., preferably by means of a Brookfield-Synchro-Lectric LVF viscosimeter. For instance, a grade CMC 400 to 800 cPs or equivalent may be used, i.e. a carboxymethyl cellulose having a viscosity (2% by weight aqueous solution) of 200 to 1500 mPas, more preferably 400 to 800 mPa·s (measured as set our before).

In other embodiments, the carboxymethyl cellulose may have a degree of substitution of 0.6 to 1.5, preferably 0.7 to 1.3.

Carboxymethyl cellulose may be present in an amount of from 0.1 to 80% by weight, preferably 1.0 to 60% by weight, in further embodiments 5.0 to 50.0% by weight and in further embodiments 15 to 40% by weight, based on the total weight of the controlled release dosage form.

The dosage forms of the present invention have proven advantageous to avoid the effect of so-called dose dumping. Dose dumping is a phenomenon that occurs, for instance, when patients do no comply with the advice to avoid the intake of alcohol concomitantly with the administration of the controlled release pharmaceutical dosage form. The intake of alcohol can accelerate the release of the dose of the active ingredient, thus leading to potentially very harmful consequences for the patient, in particular in case of analgesics and opioid analgesics. It has been found that the use of the dosage forms of the present invention in a very effective mean to avoid or at least significantly reduce the risk of dose dumping upon ingestion of alcohol.

In accordance with what has been said above, the controlled release oral dosage forms described herein are characterized by a difference of no more than 20%, preferably no more than 15% and preferably no more than 12.5% between an in vitro release rate of oxycodone at 37° C. in a solution containing 20% by weight ethanol and an in vitro release rate at 37° C. in an ethanol-free aqueous solution, when measured according to the USP Paddle Method (preferably as described in USP 34) in 900 ml aqueous buffer at 900 rpm.

Preferably, an in vitro release rate at 37° C. in an aqueous solution containing 10% by weight ethanol, and/or in an aqueous solution containing 20% by weight ethanol, and/or in an aqueous solution containing 40% by weight ethanol, has a fit factor of between 50 and 100 compared to an ethanol-free aqueous solution. The fit factor is defined as follows:

$$f_2 = 50 \cdot \log\left[\frac{100}{\sqrt{1 + \frac{\sum_{t=1}^{t=n}[\bar{R}(t) - \bar{T}(t)]^2}{n}}}\right]$$

In this equation, $f_2$ is the similarity factor, n is the number of (measurement) time points, R(t) is the mean percent reference drug dissolved at time t after initiation of the study (i.e. oxycodone in the aqueous solution without ethanol), T(t) is the mean percent test drug dissolved at time t after initiation of the study (i.e. oxycodone in ethanol containing solution). For both test and reference formulations percent dissolution should be determined.

The evaluation of the $f_2$ factor is based on the following conditions:
  A minimum of three time points (zero excluded)
  The time points should be the same for the two formulations
  Twelve individual values for every time point for each formulation
  Not more than one mean value of >85% dissolved for any of the formulations.
  The relative standard deviation or coefficient of variation of any product should be less than 20% for the first point and less than 10% from second to last time point.

Preferably, the amount of substrates in the controlled release oral dosage form ranges from 1% to 100% by weight, based on the total weight of the controlled release dosage form. In preferred embodiments, the substrates are comprised in an amount of 20% to 90% by weight, more preferably 30% to 80% by weight, based on the total weight of the controlled release dosage form.

The controlled release oral dosage forms according to the present invention, in particular when present as tablets, may further comprise one or more pharmaceutically acceptable excipients, such as fillers, binding agents, disintegrants, plasticizers, and glidants. These excipients may be included in a coating or the external phase of the tablet, in particular.

Fillers are normally used to dilute a pharmaceutical composition and provide bulk. Fillers are preferably used in tablets. Examples for preferred fillers include lactose, starch, calcium phosphate, calcium carbonate, saccharose, sugar alcohols such as mannitol, sorbitol, xylitol, and or microcrystalline cellulose. Microcrystalline cellulose is particularly preferred. Vivapur®102 or Avicel®102 are suitable commercially available examples.

In a preferred embodiment a filler mixture comprising sodium carboxymethyl cellulose and microcrystalline cellulose, preferably in a weight ratio of 3:1 to 1:3, more preferably 2:1 to 1:2 is used. A filler or mixture of fillers may be used in an amount of from 0 to 60% by weight, preferably 1 to 50% by weight, and in particular 5 to 40% by weight, based on the total weight of the controlled release oral dosage form, preferably the tablet.

Binders generally serve to enhance the integrity and stability of tablets. In addition, they may improve the suitability of pharmaceutical compositions for granulation. Binders are commonly also used for the preparation of films, such as active agent containing layers, around an inert core. Exemplary binders include synthetic polymers, such as polyvinyl pyrrolidone, vinyl pyrrolidone-vinyl acetate-copolymer, modified celluloses, such as hydroxy alkyl celluloses and mixtures thereof. A binder is typically used in an amount of 0 to 25% by weight, preferably 0.1 to 15% by weight and in further embodiments 1 to 10% by weight of the controlled release oral dosage form. Preferably hydroxypropyl methyl cellulose (HPMC) is used as binder.

A disintegrant enhances the disintegration of a dosage form, in particular a tablet, after its immersion in water or gastric juices. Suitable disintegrants include carrageenan, crospovidone and mixtures thereof. Disintegrants may be used in amounts of 0 to 25% by weight, preferably 1.0 to 20% by weight and in further embodiments 3 to 15% by weight of the controlled release oral dosage form, preferably the tablet.

The controlled release oral dosage forms may further include a glidant, such as disperse silica, such as Aerosil®, or talc. A glidant (or mixture thereof) may be comprised in an amount of from 0 to 5% by weight, for instance 0.1 to 4% by weight of the controlled release oral dosage form, preferably the tablet.

The oral controlled release dosage form may further comprise a lubricant, in particular in tablets prepared by compression. Suitable lubricants include stearic acid, magnesium stearate, adipic acid and sodium stearyl fumarate (Pruv®).

In a preferred embodiment the external phase (without coated pellets) comprises
  85 to 99.9%, preferably 90 to 98% by weight filler,
  0 to 5%, preferably 0.1 to 1.0% by weight lubricant and
  0.1 to 10%, preferably 1.0 to 5% by weight glidant,
  based on the total weight of the external phase.

Optionally, the controlled release oral dosage form according to the present invention, particularly when present in the form of a tablet, can comprise an external film for improved ease of swallowing, for protection, for colouring, for taste-masking or other purposes. Preferably, this external film does not influence the release of oxycodone to any significant extent. The external film may comprise the usual excipients known in this art for this purpose. A combination of hypromellose, talc, a colouring agent, such as titanium dioxide, and/or a polymer, such as polyethylene glycol is a preferred embodiment herein. This optional film is not counted towards the total weight of the controlled release oral dosage form herein. Expressed differently, any amount of an ingredient expressed as weight percent herein refers to the controlled release oral dosage form without this optional external film. As evident from the above, the external film is free of oxycodone in any form.

The (multi-particulate) controlled-release oral dosage form according to the present invention has the advantage that it may be divided into two or more units without impairing the controlled release of oxycodone. The controlled release oral dosage form, and in particular the tablet, may therefore comprise means facilitating its division into two or more units, such as a break-line, each of said units providing controlled release of oxycodone. The dosage form according to the present invention therefore provides for the possibility to adjust the dosage, for instance halve the dosage by breaking the tablet in two.

In preferred embodiments according to the present invention, the oxycodone salt is oxycodone hydrochloride. The dosage form may contain oxycodone in amounts of from 5 to 160 mg. If oxycodone is used as free base, the amount of 5 to 160 mg refers to the weight of the free base. If oxycodone is used in the form of a pharmaceutical acceptable salt, the amount of 5 to 160 mg refers to the weight of the salt. Preferably, the dosage form of the present invention comprises 10 mg oxycodone, 20 mg oxycodone, 40 mg oxycodone or 80 mg oxycodone, more preferably 10 mg oxycodone hydrochloride, 20 mg oxycodone hydrochloride, 40 mg oxycodone hydrochloride or 80 mg oxycodone hydrochloride.

Preferably, the dosage form of the present invention provides the following in vitro release of oxycodone, when measured according to the USP Paddle Method in 900 ml aqueous buffer at 100 rpm, 37° C. and pH 2: between 1 and 20% by weight after 2 hours, between 10 and 35% by weight after 4 hours and/or between 40 and 70% by weight after 8 hours.

As mentioned before, the dosage forms according to the present invention have surprisingly been found to have very advantageous in vivo properties despite a mean $C_{24}/C_{max}$ ratio of less than 0.6. In exemplary embodiments, at steady state the oral dosage form according to the present invention provides a mean $C_{24}/C_{max}$ of between 0.10 and 0.58, preferably between 0.30 and 0.56, for instance between 0.35 and 0.55 or 0.54 after oral administration. Preferably, in vivo parameters are determined as described in Bauer, Frömming, Führer, "Lehrbuch der Pharmazeutischen Technologie", $8^{th}$ edition, chapter 4.2.1 "Grundlagen and Methoden".

The controlled release oral dosage forms according to the present invention are preferably for the treatment of severe and very severe pain, more preferably of severe and very severe pain according to the VAS scale. In particular, the controlled release oral dosage form is suitable for patients who need continuous treatment over an extended period of time.

According to a further aspect, the present invention provides a method for preparing a controlled release oral dosage form, preferably as described above, comprising:
a) coating each of a plurality of inert cores with a layer comprising oxycodone or a pharmaceutically acceptable salt or solvent thereof,
b) coating each of the plurality of coated inert cores with a release control layer comprising a release control substance for controlling the release of oxycodone, thus forming a plurality of substrates,
c) mixing the plurality of substrates with at least one pharmaceutically acceptable excipient,
d) forming a tablet from the mixture comprising the plurality of substrates and the at least one pharmaceutically acceptable excipient.

For preferred embodiments of inert cores, preferred oxycodone forms, release controlling substances, further excipients, the substrates etc., it is referred to the explanations concerning embodiments of the dosage forms of the present invention above, which naturally equally apply to the method for preparing a controlled release dosage form according to the present invention.

Step a) may further include dissolving or suspending oxycodone or a salt thereof in a suitable solvent or solvent mixture, optionally together with a binder, such as a hydroxyalkyl cellulose, such as hydroxy propylmethyl cellulose. The solvent is preferably water, an alcohol, such as ethanol, or mixtures thereof. Preferably, the pH of the solvent is adjusted to a value which enables a complete dissolution of the oxycodone. More preferably, the pH is adjusted to a value of 2 to 6, in particular 3 to 5.

Preferably, the inert cores are sugar spheres. Preferably, oxycodone hydrochloride is used. Further preferably, the coating step a) is a coating step in a fluid bed processor wherein preferably a solution or suspension (in particular solution) of oxycodone hydrochloride and one or more excipients, such as hypromellose, are sprayed onto the inert cores. The coating solution or suspension usually comprises respectively consists of water and/or an alcohol. Preferably, the process temperature is between 30 and 60° C.

Preferably, step b) involves coating by spraying a coating solution containing the release control substance onto the coated inert cores from step a). The spraying step is preferably performed in a fluid bed processor. The fluid bed processor is preferably suitable for coating of powders, particles, inert spheres, pellets and tablets, and/or simultaneous drying. Preferably, the process temperature is between 30 and 60° C.

The solvent of the coating solution or suspension from step b) predominantly contains alcohol, i.e. the solvent used for dissolving the release controlling agent and optional further excipients contains preferably 60% or more by weight, more preferably 70% or more by weight of alcohol. A mixture of ethanol and water is particularly preferred. Furthermore, preferably ethylcellulose is used as the release controlling agent. Additional excipients may include hydroxypropyl cellulose, talc and other pharmaceutical suitable excipients.

The substrates preferably have a weight average particle diameter ($d_{50}$) of 50 to 1000 µm, in preferred embodiments 100 to 800 µm, in further embodiments 150 to 600 µm, as measured by sieve analysis, such as by means of a Retsch Siebmaschine AS 300 control. The thickness of the release control layer is preferably in a range of from 0.1 to 200 µm, preferably 0.5 to 100 µm, and most preferably 1.0 to 50 µm.

According to a further aspect, the present invention encompasses:

A controlled release oral dosage form, preferably a tablet, for administration of oxycodone once a day, comprising
a plurality of substrates, wherein each substrate comprises a core containing oxycodone or a pharmaceutically acceptable salt or solvate thereof and a release control layer containing a release control substance for controlling the release of oxycodone from the substrate comprising oxycodone,
wherein the oxycodone containing core comprises a layer comprising oxycodone disposed on an inert core and/or wherein the release control substance is a hydrophobic polymer, preferably an alkyl cellulose, such as ethyl cellulose.

As set out before, the dosage form is a multi-particulate dosage form.

In preferred embodiments, the controlled release oral dosage form is a tablet and the plurality of substrates is contained in an external phase of at least one pharmaceutically acceptable excipient. Preferably, said external phase comprises cellulose derivatives, in particular croscarmellose or pharmaceutical acceptable salts thereof, as described before.

The embodiments and properties set out above, in particular the in vitro and in vivo properties, preferably equally apply to this aspect of the invention.

A particularly preferred embodiment of the present invention comprises one or more of the following features:

controlled-release tablet for administration of oxycodone once a day, which is a multi-particulate dosage form, a plurality of substrates, each substrate comprises a core containing oxycodone or a pharmaceutically acceptable salt or solvate thereof and a release-control layer containing a release-control substance for controlling the release of oxycodone from the substrate comprising oxycodone, wherein the oxycodone containing core comprises a layer comprising oxycodone disposed on an inert core, the inert cores preferably being saccharose cores, 90% of the inert cores having a particle size in the range of 200 to 400 μm, the oxycodone-comprising layer comprising oxycodone in the form of its HCl salt, the oxycodone-comprising layer comprising at least one of HPMC (binder) and talc (glidant), the HPMC having a viscosity <100 mPa·s, more preferably <50 mPa·s and most preferably <10 mPa·s (measurement conditions as before), the oxycodone-comprising layer having a thickness in the range of 10 to 400 μm, more preferably 100 to 300 μm (90% of the particles, as determined by sieve analysis), wherein the release control substance is a hydrophobic polymer, preferably an alkyl cellulose, most preferably ethyl cellulose, wherein the release-control layer further comprises at least one of hydroxypropyl cellulose, propylene glycol and talc, the hydroxypropyl cellulose having a viscosity (10% aqueous solution, 25° C.) of 10 to 3000 mPa·s, more preferably 100 to 1000 mPa·s, for instance 300 to 600 mPa·s, the release-control layer preferably having a (mean) thickness of less than 500 μm, more preferably less than 250 μm, such as less than 150 μm (90%, determined by sieve analysis relative to the oxycodone-coated inert cores)

the plurality of substrates being contained in an external phase, the external phase comprising at least one of carmellose sodium, microcrystalline cellulose, colloidal anhydrous silica and magnesium stearate, carmellose sodium having a viscosity (2% aqueous solution, 25° C.) of 400 to 800 mPa·s (measured as set our before), microcrystalline cellulose having a particle size distribution, as determined by air jet sieving, of at most 25, 15 or 10%>250 μm and/or at least 30, 40 or 45%>75 μm and/or at least 50, 60 or 70%>30 μm.

It is further preferred that the tablet of the present invention comprises: oxycodone-containing cores comprising 1 to 30 wt. %, preferably 2 to 20 wt. %, more preferably 3 to 10 wt. % neutral pellets, 1 to 40 wt. %, preferably 5 to 20 wt. %, more preferably 10 to 15 wt. % oxycodone, in particular oxycodone hydrochloride, 0.01 to 10 wt. %, preferably 0.1 to 5 wt. %, more preferably 0.5 to 3 wt. % binder, and 0 to 10 wt. %, preferably 0.1 to 5 wt. %, more preferably 0.5 to 3 wt. % glidant, said cores being coated with a release-control layer comprising 1 to 40 wt. %, preferably 3 to 20 wt. %, more preferably 7 to 15 wt. % release-control substance, 0.01 to 10 wt. %, preferably 0.1 to 6 wt. %, more preferably 1 to 4 wt. % pore builder, 0 to 10 wt. %, preferably 0.1 to 6 wt. %, more preferably 1 to 4 wt. % plasticiser, 0 to 15 wt. %, preferably 0.1 to 10 wt. %, more preferably 2 to 5 wt. % glidant, and an external phase comprising 20 to 85%, preferably 40 to 75%, more preferably 50 to 65% filler, 0 to 3 wt. %, preferably 0.001 to 2.0 wt. %, more preferably 0.1 to 0.5 wt. % lubricant and 0 to 5 wt. %, preferably 0.1 to 5 wt. %, more preferably 0.5 to 2.0 wt. % glidant, wherein all wt. % are based on the total weight of the tablet (without film coating).

The tablets of the present invention preferably have a tablet height of from 2 to 5 mm, more preferably 3 to 4 mm. Preferably, the tablets have a hardness of 40 to 300 N, more preferably of 50 to 200 N.

Tablets with a combination of several of the above features have been found to be particularly advantageous: They provide good clinical efficacy, not least due to providing an advantageous dissolution profile without the need to include an immediate release portion of oxycodone. They can be broken or divided without affecting the release of drug from the tablet. Dose dumping phenomena do not occur.

The invention will be further described by way of exemplary embodiments with reference to the Figures wherein.

EXAMPLES

Example 1

Preparation of Tablets Containing 10 Mg Oxycodone

Step 1:

A spraying suspension is prepared from the following ingredients:

| | |
|---|---|
| Purified water | 20.00 kg |
| Ethanol 96% | 6.80 kg |
| Hypromellose | 0.40 kg |
| Talc | 0.40 kg |
| Hydrochloric acid 0.1 N | q.s. |
| Oxycodone hydrochloride | 4.00 kg |

A spraying suspension is prepared by successively dissolving hypromellose and oxy-codon hydrochloride in a large part of the preheated purified water. Ethanol 96% is added to this solution under stirring. Talc is suspended in the remaining part of water, homo-genized, and added to the oxycodone containing solution. The pH of the resulting suspension is adjusted using HCl in order to keep the oxycodone hydrochloride in solution.

2.00 kg sugar spheres (saccharose, particle size range (90%) 200 to 400 μm are filled into a fluid-bed processor with a bottom-spray nozzle and pre-heated. The spraying suspension is then sprayed onto the sugar spheres in the fluid-bed processor, thus preparing a plurality of sugar spheres having a layer of oxycodone coated thereupon. The coated sugar spheres are then sieved through a 0.6 mm sieve (vibration sieve or equivalent).

Step 2:

A coating solution is prepared from the following ingredients:

| | |
|---|---|
| Ethanol 96% | 45.55 kg |
| Water, purified | 13.19 kg |
| Ethylcellulose | 2.33 kg |
| Hydroxypropyl cellulose (Klucel ® EF) | 0.49 kg |
| Propylene glycol | 0.48 kg |
| Talc | 0.70 kg |

Hydroxypropyl cellulose is added to the purified water and mixed until the solution is clear. Ethylcellulose and ethanol are then added to the solution. The solution is stirred and becomes opalescent. Finally, propylene glycol is added and the solution is continuously stirred until it is clear.

The coated sugar spheres from Step 1 are filled into a fluid-bed processor and pre-heated. The coated solution prepared as indicated above is sprayed onto the coated sugar spheres. The substrates obtained thereby as then sieved through a 0.710 mm sieve.

Step 3:

The following ingredients are dry mixed to a blend:

| | |
|---|---|
| Substrates from Step 2 | 10.80 kg |
| Carmellose sodium (CMC 400-800 cPs) | 9.60 kg |
| Microcrystalline cellulose | 9.350 kg |
| Colloidal anhydrous silica | 0.35 kg |
| Magnesium stearate | 0.30 kg |

The resulting dry blend is then compressed to tablets.

Step 4 (Optional):

A tablet coating suspension is made from the following ingredients:

| | |
|---|---|
| Titanium dioxide | 0.42 kg |
| Hypromellose | 1.16 kg |
| Macrogol 6000 | 0.26 kg |
| Talc | 0.16 kg |
| Water, purified | 14.50 kg |

34.0 kg tablets are film coated with the tablet coating suspension.

Figure 3:
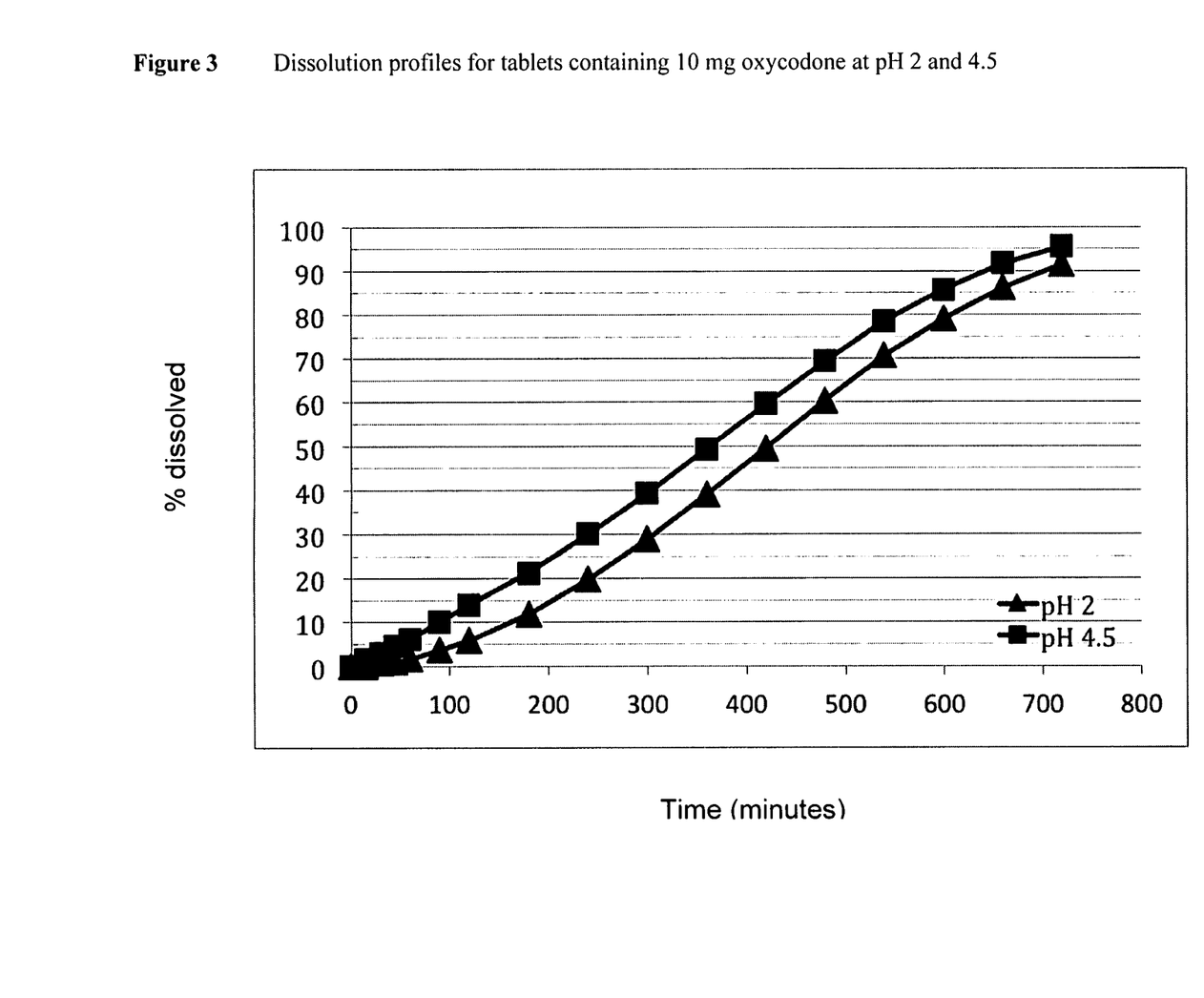
FIG. 3 shows the dissolution profile of a 10 mg containing oxycodone tablet at pH 2 and pH 4.5.
Figure 4:
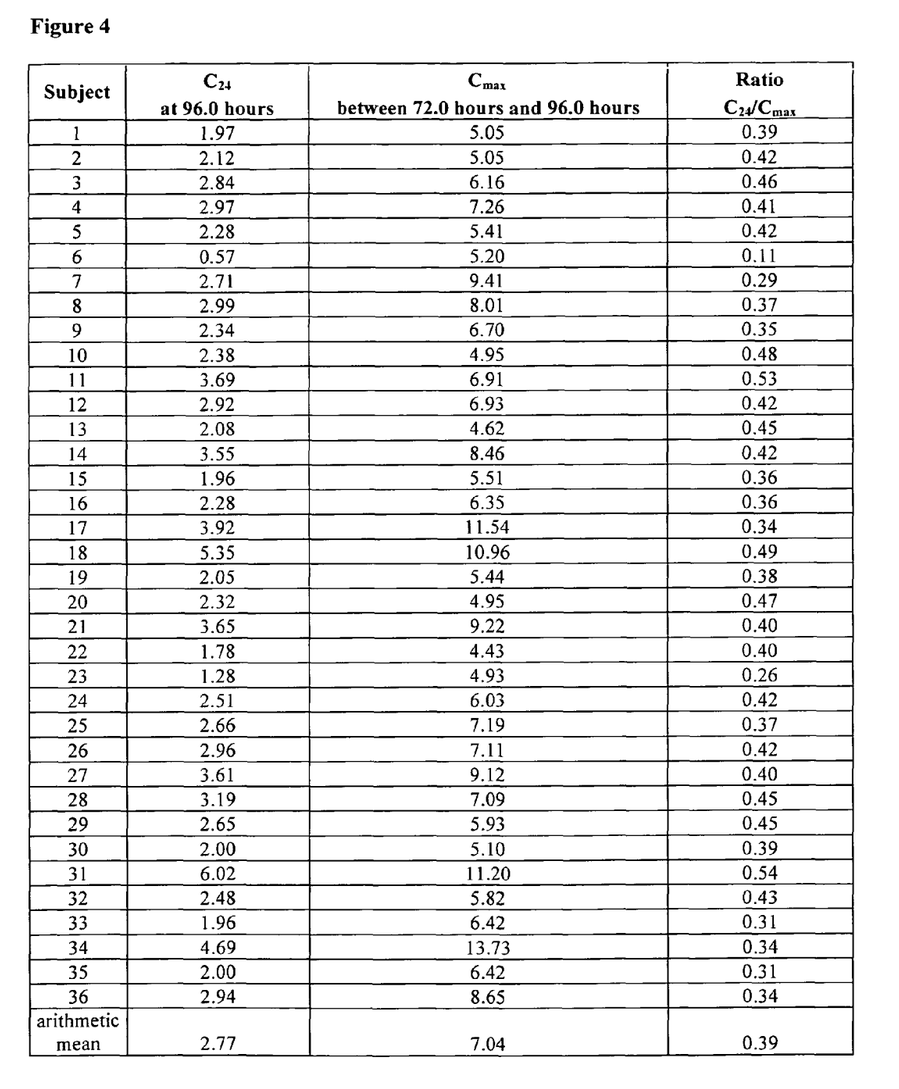
FIG. 4 represents a table listing the $C_{max}$ and $C_{24}$ values as well as their ratios in 36 subjects taking part in a steady state study involving tablets containing 10 mg oxycodone according to the invention.

The dissolution profiles of the 10 mg tablets are in accordance with the present invention, as apparent from FIG. 3. FIG. 4 shows the $C_{max}$ and $C_{24}$ values as well as their ratios from 36 subjects taking part in a steady state study involving tablets containing 10 mg oxycodone according to Example 1.

Example 2

Preparation of Tablets Containing 20 Mg Oxycodone

The tablets of Example 2 are prepared in the same manner as those in Example 1. Except, in the 20 mg tablets, double the amount of oxycodone hydrochloride and excipients (including in this context release controlling layer, solvents etc.) is employed.

Figure 1A:
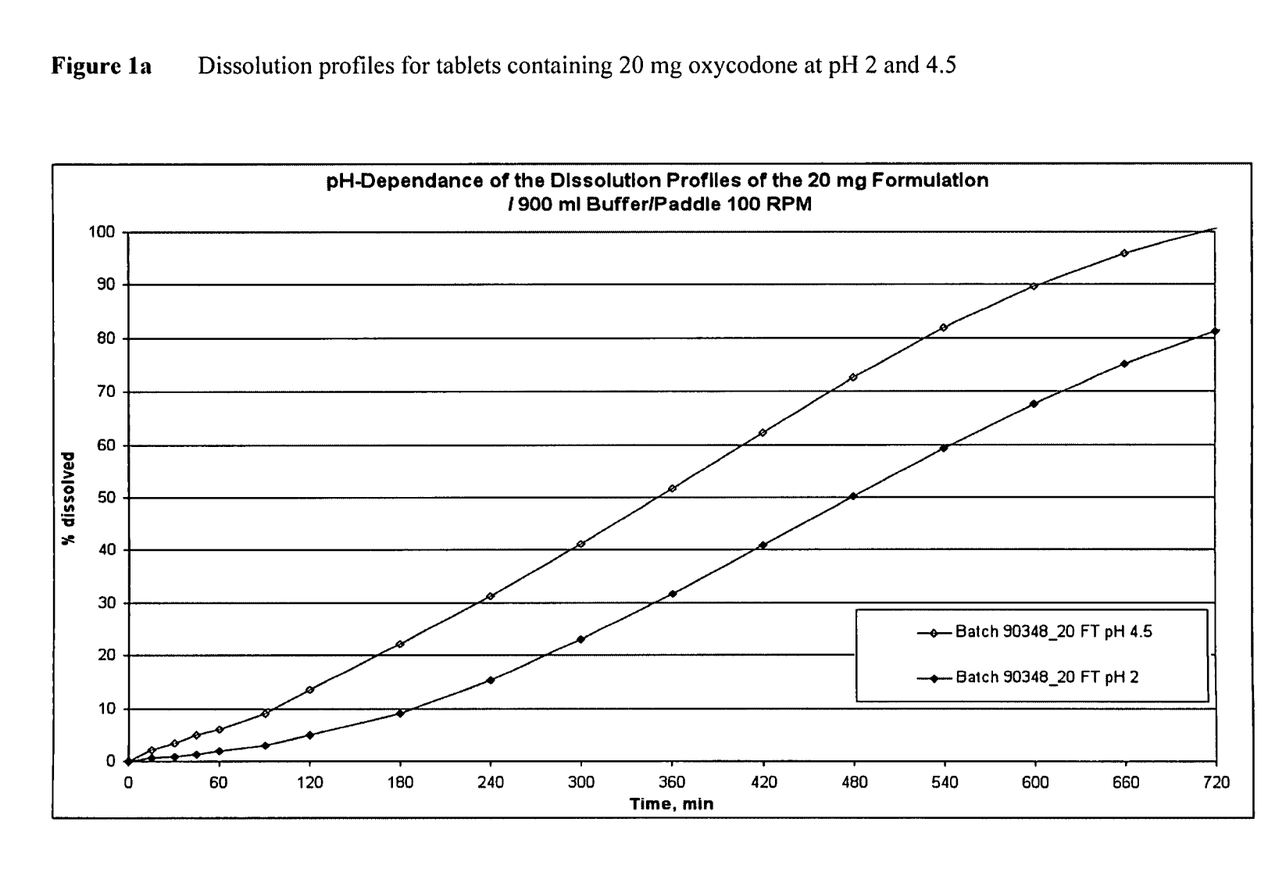
FIG. 1a shows the dissolution profile of a 20 mg containing oxycodone tablet at pH 2 and pH 4.5.
Figure 1B:
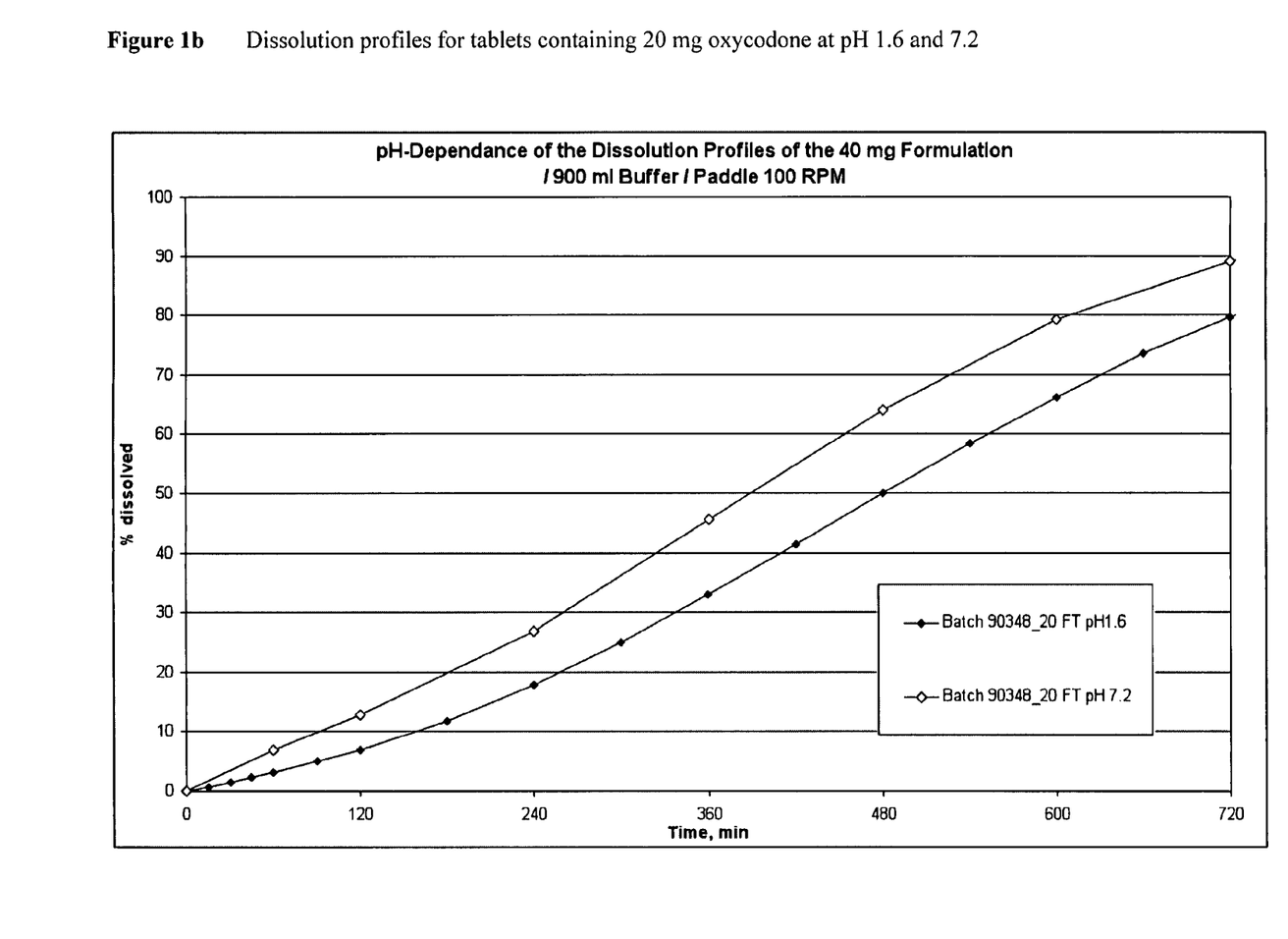
FIG. 1b shows the dissolution profile of a 20 mg containing oxycodone tablet at pH 1.6 and pH 7.2.

The dissolution profiles of the 20 mg tablets according to Example 2 are shown in FIGS. 1a and b. The dissolution profiles were measured using the USP Paddle Method at 37° C.

Example 3

Preparation of Tablets Containing 40 Mg Oxycodone

The tablets of Example 3 are prepared in the same manner as those in Example 1. Except, in the 40 mg tablet, four times the amount of oxycodone hydrochloride and excipients (including in this context release controlling layer, solvents etc.) is used.

Figure 2A:
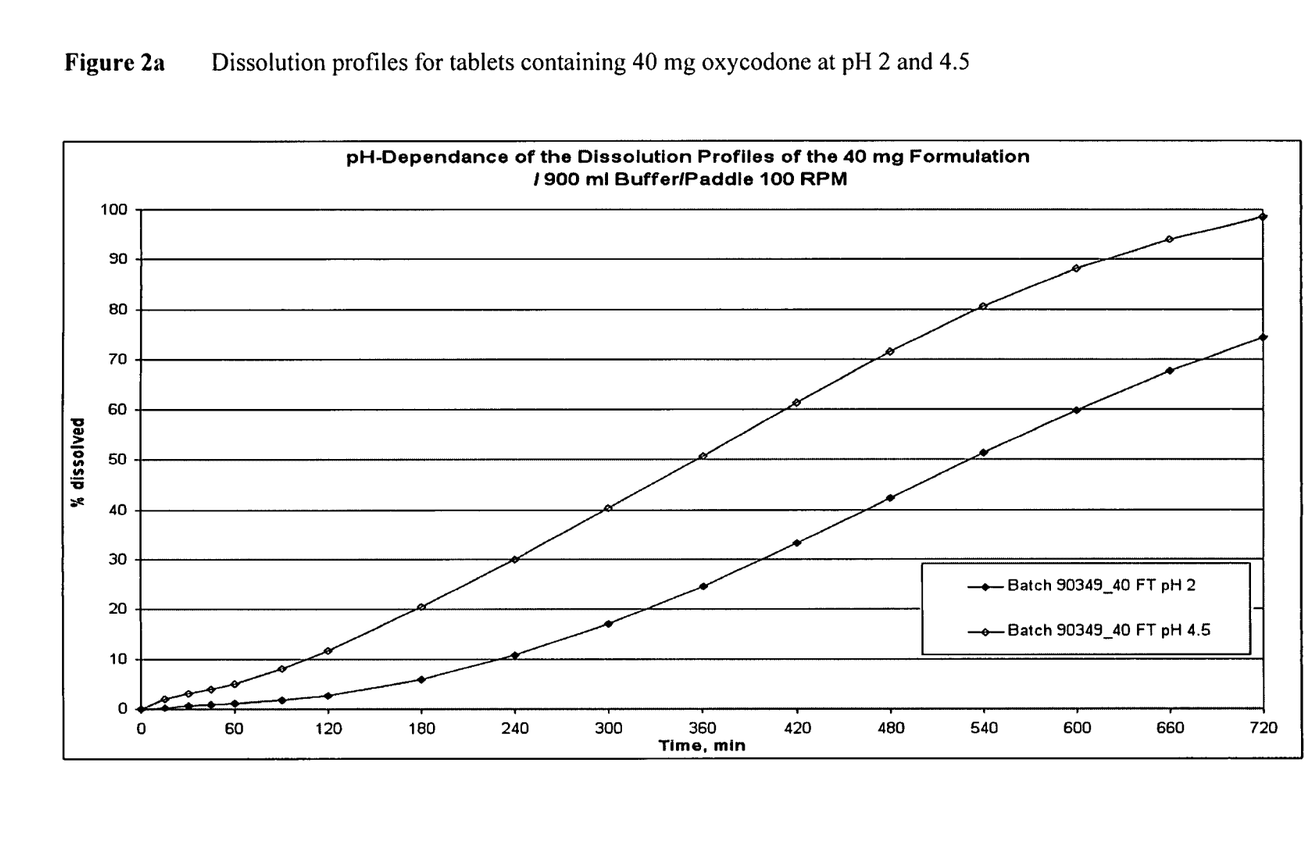
FIG. 2a shows the dissolution profile of a 40 mg containing oxycodone tablet at pH 2 and pH 4.5.
Figure 2B:
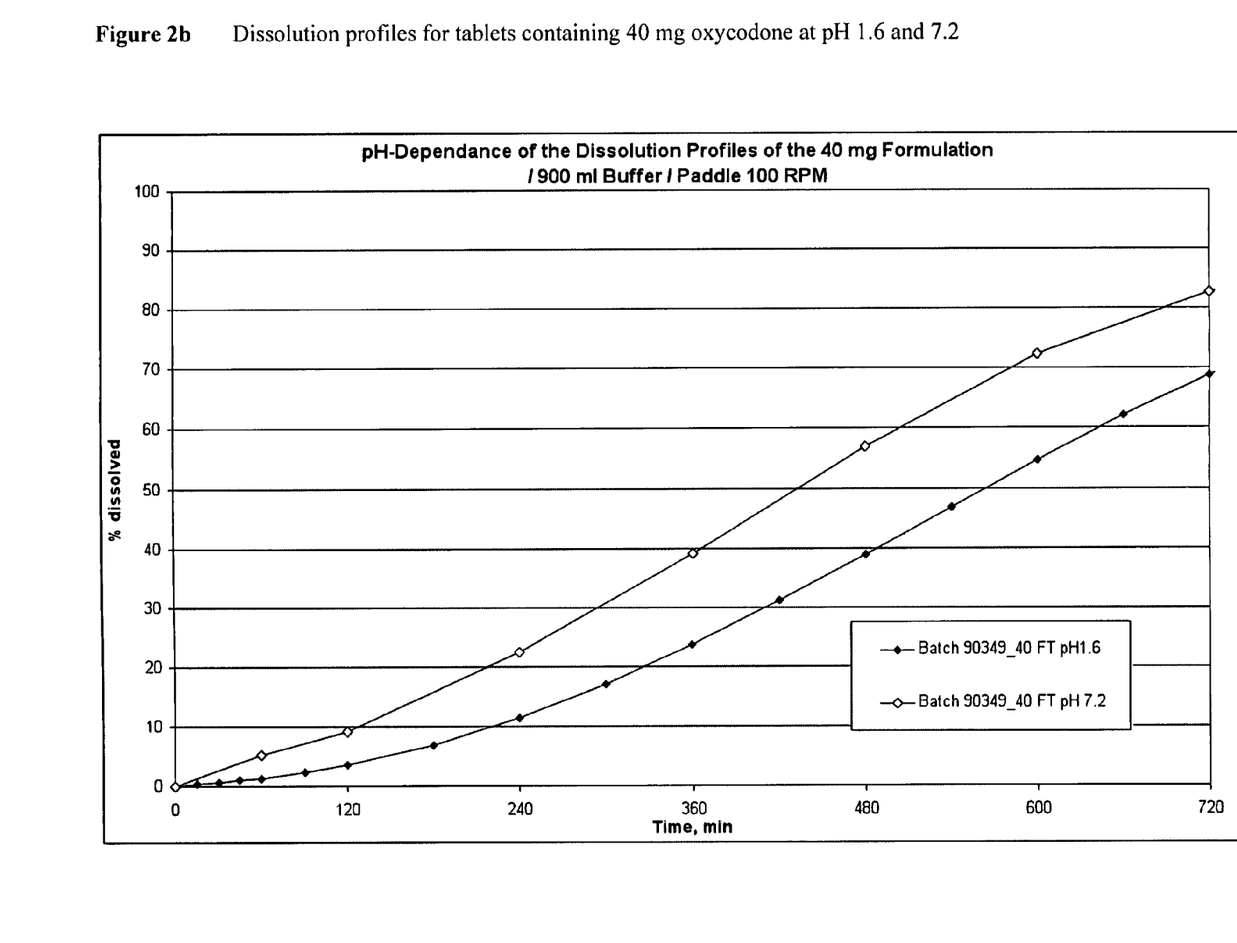
FIG. 2b shows the dissolution profile of a 40 mg containing oxycodone tablet at pH 1.6 and pH 7.2.

The dissolution profiles of the 40 mg tablets according to Example 3 are shown in FIGS. 2a and b. The dissolution profiles were measured using the USP Paddle Method at 37° C.

Figure 5:
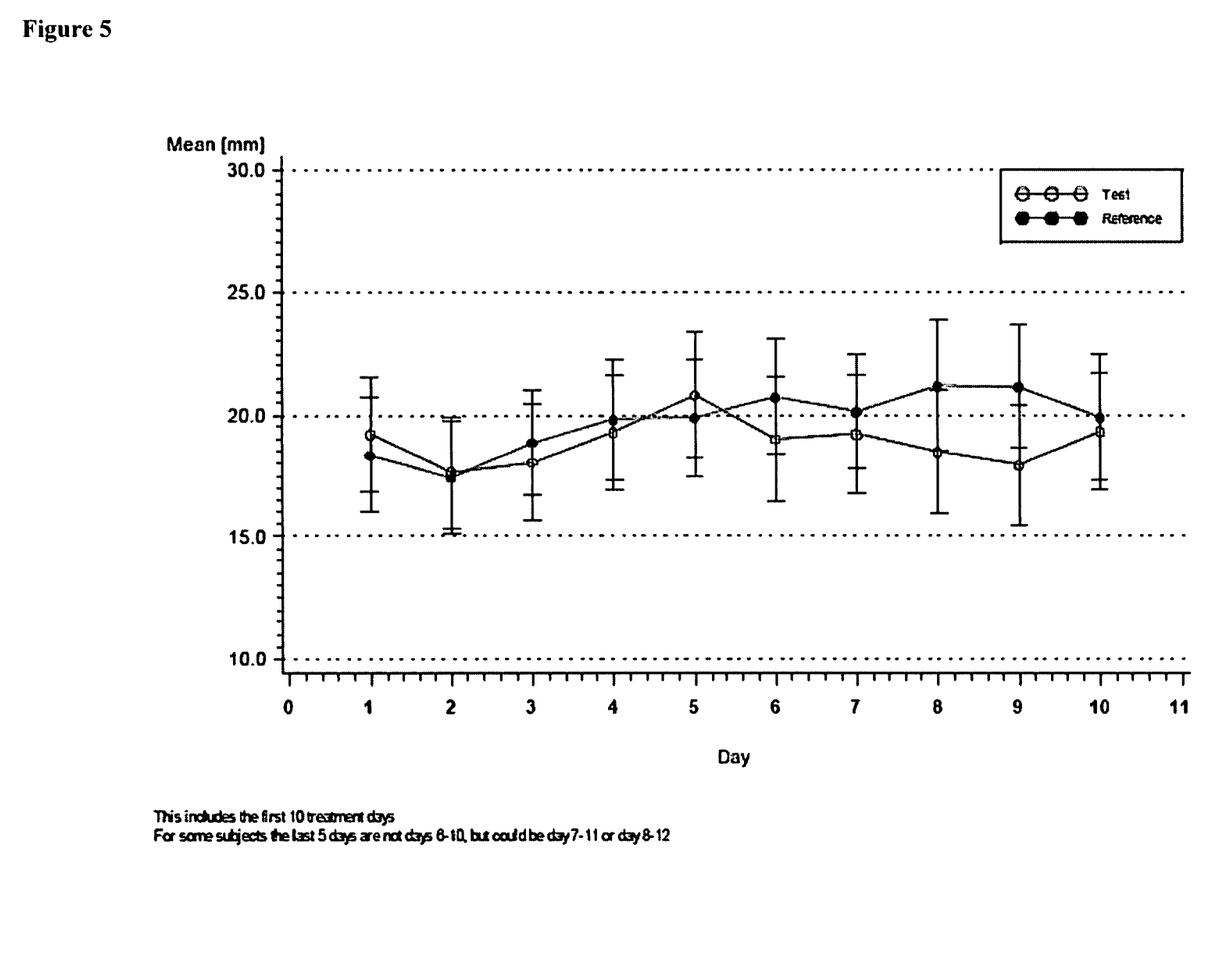
FIG. 5 illustrates the efficacy of dosage forms according to the present invention administered once a day in comparison to commercially available tablets administered twice a day.

FIG. 5 illustrates results of a randomized, double-blind cross-over Phase III study to investigate the efficacy and safety of oxycodone tablets according to the present invention administered once a day (designated "test" in FIG. 5) in comparison to twice daily administration of Oxygesic® 20-120 mg tablets (designated "reference" in FIG. 5) in patients with chronic cancer pain/chronic pain. As apparent from FIG. 5, which illustrates the mean current pain intensity score (on a 0-100 mm VAS scale), the pain relief provided by the dosage forms according to the present invention when administered once a day closely resembles that obtained by twice daily administration of conventional oxycodone tablets.

The invention claimed is:

1. A multi-particulate controlled-release oral dosage form for use in the treatment of chronic pain by administration of oxycodone once a day, comprising a plurality of substrates comprising oxycodone or a pharmaceutically acceptable salt or solvate thereof, each substrate comprising a release-control substance for controlling the release of oxycodone of the salt or solvate thereof, wherein each substrate comprises an oxycodone-containing core and a release-control layer containing the release-control substance for controlling the release of oxycodone from the substrate, wherein at steady state the oral dosage form provides a mean $C_{24}/C_{max}$ of between 0.30 and 0.50 after oral administration;

wherein the core comprises a layer comprising oxycodone coated on an inert core and/or wherein the release control substance is a polymer selected from the group consisting of cellulose acetate phthalate, polyvinyl pyrrolidone, polyvinyl alcohol, polyvinyl acetate, polyvinyl chloride, nylon, polyamide, polyethylene oxide, polylactide-co-glycolide and mixtures thereof, and ethyl cellulose; and wherein the plurality of substrates is contained in an external phase of at least one pharmaceutically acceptable excipient, wherein the release-control layer comprises
40 to 80 wt. % release control substance,
1 to 25 wt. % pore builder
1 to 25 wt. % plasticiser, and optionally
5 to 30 wt. % glidant
based on the total weight of the release-control layer.

2. The controlled-release oral dosage form according to claim 1, wherein the carboxymethyl cellulose, optionally in the form of a salt, as a pharmaceutically acceptable excipient.

3. The controlled-release oral dosage form according to claim 1, which is a tablet.

4. The controlled-release oral dosage form according to claim 1, further comprising means facilitating division into two or more units, each of said units providing controlled-release of oxycodone.

5. The controlled-release oral dosage form according to claim 1, wherein the oxycodone salt is oxycodone hydrochloride.

6. The controlled release oral dosage form according to claim 1, providing an in vitro release of oxycodone, when measured according to the USP Paddle Method in 900 ml aqueous buffer at 100 rpm and pH 2 of between 1 and 20% by weight after 2 hours, between 10 and 35% by weight after 4 hours and/or between 40 and 70% by weight after 8 hours.

7. The controlled-release oral dosage form according to claim 1 characterized by a difference of no more than 20% between an in vitro release rate at 37° C. in a solution containing 20% by weight ethanol and an in vitro release rate at 37° C. in an ethanol-free aqueous solution, when measured according to the USP Paddle Method in 900 ml aqueous buffer at 100 rpm.

8. The controlled-release oral dosage form according to claim 1, wherein the dosage forms comprises 10 mg, 20 mg, 40 mg or 80 mg oxycodone hydrochloride.

9. A controlled-release tablet for administration of oxycodone once a day, comprising
 a plurality of substrates comprising oxycodone or a pharmaceutically acceptable salt or solvate thereof,
 wherein each substrate comprises an oxycodone-containing core and a release-control layer coated upon the core and containing a release-control substance for controlling the release of oxycodone from the substrate,
 the plurality of substrates being contained in an external phase of at least one pharmaceutically acceptable excipient, wherein the external phase comprises carboxymethyl cellulose, optionally in the form of a salt, as a filler, and
 wherein at steady state the controlled-release tablet provides a mean $C_{24}/C_{max}$ ratio of between 0.30 and 0.50 after oral administration,
 wherein the oxycodone-containing core comprises
 1 to 30 wt.% neutral pellets,
 1 to 40 wt.% oxycodone,
 0.01 to 10 wt.% binder, and
 0 to 10 wt.% glidant,
 the release-control layer comprises
 1 to 40 wt.% release-control substance,
 0.01 to 10 wt.% pore builder,
 0.01 to 10 wt.% plasticiser,
 0 to 15 wt.% glidant,
 and
 the external phase comprises
 20 to 85 wt.% filler,
 0 to 3 wt.% lubricant and
 0 to 5 wt.% glidant,
 wherein all wt.% are based on the total weight of the tablet,
 wherein the release control substance is selected from the group consisting of cellulose acetate phthalate, polyvinyl pyrrolidone, polyvinyl alcohol, polyvinyl acetate, polyvinyl chloride, nylon, polyamide, polyethylene oxide, polylactide-co-glycolide and mixtures thereof, and ethyl cellulose.

10. A method for preparing a controlled-release oral dosage form according to claim 9, comprising:
 a) coating each of a plurality of inert cores with a layer comprising oxycodone or a pharmaceutically acceptable salt or solvent thereof,
 b) coating each of the plurality of coated inert cores with a release-control layer comprising the release-controlling substance for controlling the release of oxycodone, thus forming the plurality of substrates,
 c) mixing the plurality of substrates with carboxymethyl cellulose, optionally in the form of a salt, and optionally at least one further pharmaceutically acceptable excipient,
 d) forming a tablet from the mixture comprising the plurality of substrates and the at least one pharmaceutically acceptable excipient.

11. The tablet according to claim 9, wherein said oxycodone is oxycodone hydrochloride.

* * * * *